United States Patent
McMichael

(10) Patent No.: US 10,213,480 B2
(45) Date of Patent: Feb. 26, 2019

(54) METHOD OF INHIBITING MICROGLIAL CELL MIGRATION AND TREATING TRAUMATIC BRAIN INJURY

(71) Applicant: BEECH TREE LABS, INC., Delanson, NY (US)

(72) Inventor: John McMichael, Delanson, NY (US)

(73) Assignee: BEECH TREE LABS, INC., Delanson, NY (US)

( * ) Notice: Subject to any disclaimer, the term of this patent is extended or adjusted under 35 U.S.C. 154(b) by 0 days.

(21) Appl. No.: 15/725,186

(22) Filed: Oct. 4, 2017

(65) Prior Publication Data

US 2018/0028602 A1    Feb. 1, 2018

Related U.S. Application Data

(63) Continuation-in-part of application No. PCT/US2016/026330, filed on Apr. 7, 2016.

(60) Provisional application No. 62/144,590, filed on Apr. 8, 2015.

(51) Int. Cl.
| | |
|---|---|
| *A61K 38/16* | (2006.01) |
| *G01N 33/50* | (2006.01) |
| *A61K 9/00* | (2006.01) |
| *C07K 16/12* | (2006.01) |

(52) U.S. Cl.
CPC ............ *A61K 38/164* (2013.01); *A61K 9/006* (2013.01); *C07K 16/1275* (2013.01); *G01N 33/5058* (2013.01)

(58) Field of Classification Search
CPC combination set(s) only.
See application file for complete search history.

(56) References Cited

U.S. PATENT DOCUMENTS

| | | |
|---|---|---|
| 5,576,289 A | 11/1996 | McMichael |
| 5,736,508 A | 4/1998 | McMichael |
| 5,798,102 A | 8/1998 | McMichael et al. |
| 6,998,121 B2 | 2/2006 | McMichael |
| 7,196,058 B2 | 3/2007 | McMichael et al. |
| 7,629,058 B2 | 12/2009 | Takayanagi et al. |
| 8,980,826 B2 | 3/2015 | McMichael |
| 2007/0087437 A1 | 4/2007 | Hu |
| 2008/0182789 A1 | 7/2008 | McMichael |
| 2010/0144602 A1* | 6/2010 | McMichael |
| 2013/0052184 A1 | 2/2013 | Chang et al. |
| 2013/0243696 A1 | 9/2013 | Wang et al. |
| 2014/0120191 A1 | 5/2014 | McMichael |

OTHER PUBLICATIONS

Watters et al., J Neurosci Res., 81:447-455 (Year: 2005).*
Button et al., Nat. Rev. Neurosci., 14:365-376 (Year: 2013).*
Johnson et al., "Binding of Cholesterol by Sulfhydryl-Activated Cytolysins," *Infection and Immunity*, vol. 27, No. 1, pp. 97-101 (1980).
Alouf et al., "Streptococcal Toxins (Streptolysin O, Streptolysin S, Erythrogenic Toxin)," *Pharmac. Ther.*, vol. 11, pp. 661-717 (1984).
Bhakdi et al., "Mechanism of Membrane Damage by Streptolysin-O," *Infection and Immunity*, pp. 52-60(1985).
Razin et al., "Protein kinases C-β and C-ε link the mast cell high affinity receptor for IgE to the expression of c-f08 and c-jun," *Proc. Nat'l. Acad. Sci.*, vol. 91, pp. 722-7726 (1994).
Mannix et al., "Clinical Correlates in an Experimental Model of Repetitive Mild Brain Injury," *Annals of Neurology*, pp. 65-75 (2013).
Sayer N. A., et al., "Characteristics and Rehabilitation Outcomes Among Patients with Blast and Other Injuries Sustained During the Global War on Terror," *Arch Phys Med. Rehabil.*, vol. 89, pp. 163-170 (2008).
Hadass, O. et al., "Selective Inhibition of Matrix Metalloproteinase-9 Attenuates Secondary Damage Resulting from Severe Traumatic Brain Injury," PLOS One 8, (2013).
Mori, T. et al., "Downregulation of matrix metalloproteinase-9 and attenuation of edema via inhibition of ERK mitogen activated protein kinase in traumatic brain injury," *J. Neurotrauma* 19, 1411-1419 (2002).
Roberts, D.J., et al., "A prospective evaluation of the temporal matrix metalloproteinase response after severe traumatic brain injury in humans," *J. Neurotrauma* 30, 1717-1726 (2013).
Wang, X., et al., "Effects of matrix metalloproteinase-9 gene knock-out on morphological and motor outcomes after traumatic brain injury," *J. Neurosci.* 20, 7037-7042 (2000).
Y. Koyama, "Signaling molecules regulating phenotypic conversions of astrocytes and glial scar formation in damaged nerve tissues," *Neurochemistry International* 78, pp. 35-42 (2014).
Yasir N. Jassam et al., "Neuroimmunology of Traumatic Brain Injury: Time for a Paradigm Shift," *Neuron* 95, pp. 1246-1265 (2017).
International Search Report and Written Opinion for Application No. PCT/US2016/026330, dated Jul. 6, 2016.
Fujioka et al., "Neural Functions of Matrix Metalloproteinases: Plasticity, Neurogenesis, and Disease," *Biochemistry Research International*, pp. 1-8 (2012).
Rosell et al., "Increased Brain Expression of Matrix Metalloproteinase-9 After Ischemic and Hemorrhagic Human Stroke," *Stroke*, pp. 1399-1406 (2006).
Mamber et al., "Effects of Streptolysin O on Extracellular Matrix Gene Expression in Normal Human Epidermal Keratinocytes," *Dose-Response*, pp. 554-578 (2011).

* cited by examiner

*Primary Examiner* — Kimberly Ballard
*Assistant Examiner* — Stacey N MacFarlane
(74) *Attorney, Agent, or Firm* — Marshall, Gerstein & Borun LLP

(57) ABSTRACT

Disclosed herein is a method of inhibiting microglial cell migration in the brain of a mammalian subject in need thereof, including subjects suffering from the symptoms of traumatic brain injury (TBI) and subjects suffering from a hematoma in the brain comprising administering an effective amount streptolysin O (SLO) wherein microglial migration is inhibited providing therapeutic benefits to subjects suffering from diseases characterized by microglial cell migration and activation.

9 Claims, 1 Drawing Sheet

METHOD OF INHIBITING MICROGLIAL CELL MIGRATION AND TREATING TRAUMATIC BRAIN INJURY

CROSS-REFERENCE TO RELATED APPLICATION

This application is a continuation-in-part of International Application No. PCT/US16/26330, filed Apr. 7, 2016, which claims the benefit of priority to U.S. Provisional Patent Application No. 62/144,590, filed Apr. 8, 2015, the disclosures of which are incorporated herein by reference in their entirety.

BACKGROUND OF THE INVENTION

Migration and activation of microglial cells mediates a number of disease processes in the brain including neurodegenerative diseases such as those associated with Tau pathologies and Beta-amyloid diseases, CNS injuries including spinal cord injuries and traumatic brain injury (TBI) as well as neurodevelopmental disorders and conditions such as stroke, Amyotrophic lateral Sclerosis and cerebral ischemia.

There remains interest in therapeutic agents and methods for inhibiting the migration and activation of microglial cells involved in cerebral ischemia or cerebral inflammation. While the brain is considered a site of relative immune privilege there is recognition that CNS tissue injury is mediated by types of inflammatory responses including those involving microglial cells.

A traumatic brain injury (TBI) is a disruption of function in the brain that results from a blow or jolt to the head or penetrating head injury. TBI is heterogeneous in its cause and can be seen as a two-step event: 1) a primary injury, which can be focal or diffuse, caused by mechanical impact, that results in primary pathological events such as hemorrhage and ischemia, tearing of tissue and axonal injuries; 2) a secondary injury such as diffuse inflammation, cell death and gliosis, which is a consequence of the primary one. This secondary injury starts immediately after injury and can continue for weeks, and is thought to involve an active inhibition of neural stem cell activity. Collectively, these events lead to neurodegeneration.

A large fraction of TBI is mild, and thus may go undiagnosed immediately after injury. Undiagnosed and untreated TBI presents a risk because some signs and symptoms may be delayed from days to months after injury, and may have significant impact on the patient's physical, emotional, behavioral, social, or family status if untreated, and may result in a functional impairment. Because secondary damage from the injury continues after the initial impact, early treatment (and thus rapid diagnosis), particularly point-of-care treatment, is desirable. An ideal therapy for TBI would reduce the injury infarct size as well as limiting the secondary inflammatory responses. In the U.S., about 1.5 million people per year suffer a traumatic brain injury (TBI), reflecting physical damage to the brain that compromises brain function either temporarily or permanently. Of the total number so injured, some 50,000 die while another 80,000 have some degree of disability. The leading causes of TBI are accidents (auto, bicycle, pedestrian), assault, and sport-related injury.

Head injuries are described as being open or closed. Open head injuries involve penetration of the scalp and skull by bullets, sharp objects, or skull fractures resulting in laceration of brain tissue.

Closed injuries occur when rapid brain acceleration or deceleration results from shaking, crash, falls or other sudden insult. This rapid acceleration or deceleration can damage the brain at the point of contact (coup) or opposite that point (countercoup). The temporal and frontal lobes are most susceptible to damage, which can involve axon and/or blood vessel tearing. Torn blood vessels can leak and lead to hematomas, contusions, or intracerebral and subarachnoid hemorrhages.

Concussion is described as an immediate, but transient, loss of consciousness accompanied by a short period of amnesia. However, the TBI victim may appear to be dazed, disoriented or confused. A concussion may be accompanied by convulsions, hypotension, fainting and facial pallor. These signs and symptoms are usually short-lived in cases of single, uncomplicated concussion.

Traumatic brain injury can be both acute, occurring recently, as well as of the chronic form resulting from the long term consequences of such acute brain injuries including the effects of inflammation and scarring on the brain tissue.

Football and soccer players appear to suffer a significantly higher frequency of concussion than athletes in other sports. Professional football players in the National Football League (NFL) have recently brought to the public's attention the long-term consequences of multiple concussions incurred during their playing days. Included as frequently reported signs are loss of cognition, decreased communicative skills, compromised emotional stability, poor coordination, memory loss and dementia.

An increasingly prevalent subset of TBI is blast-induced or blast TBI (bTBI). With the increasing use of explosives, including improvised explosive devices (IEDs) in the global war on terrorism, bTBI is also increasing. Such injuries are often referred to as the hallmark injury of the wars in Iraq and Afghanistan, and affect both military and civilian workers in battle zones. Blast injuries are the most common cause of TBI in US soldiers in combat and a major cause of disability among service members.

Blast injuries can result in the full spectrum of closed and penetrating TBIs (mild, moderate, and severe). Mild and moderate TBI's are more prevalent than severe injuries in the current military conflict due to the vast improvement in protective gear, leading to an increase in survivors of bTBI.

Blast injuries are defined by four potential mechanism dynamics: (1) Primary Blast Atmospheric over-pressure followed by under-pressure or vacuum; (2) Secondary Blast Objects placed in motion by the blast hitting the subject; (3) Tertiary Blast: Subject being placed in motion by the blast and (4) Quaternary Blast: Other injuries from the blast such as burns, crush injuries, amputations, toxic fumes.

bTBI are typically closed-head injuries and are more complex than other forms of TBI, with multiple mechanisms of injury including shockwave transmission through the skull and sensory organs of the head. In a patient sample seen in the Department of Veterans Affairs (VA) polytrauma system, the pattern of injuries was different among those with injuries due to blasts versus other mechanisms. Injuries to the face (including eye, ear, oral, and maxillofacial), penetrating brain injuries, symptoms of posttraumatic stress, and auditory impairments are more common in blast-injured patients than in those with war injuries of other etiologies. Sayer N A et al. (2008) Arch Phys Med. Rehabil. January; 89:163-70. Accordingly there remains an interest in therapies which might be effective in treating one or more symptoms of both acute and chronic traumatic brain injury.

Related to but not limited to traumatic brain injuries are hematomas in the brain. Hematomas are broadly defined as collections of blood outside of blood vessels and when they occur in the brain they are associated with the activation and migration of microglial cells to the location of the injury.

Streptolysin O (SLO) is one of a group of filterable hemolysins derived from Group A beta-hemolytic streptococci. Specifically, streptolysin O is a 60-kD peptide, which is hemolytic in its reduced state, but is inactivated upon oxidation (Johnson et al., Infect. Immun., 27:97-101, 1980; Alouf et al., Pharmacol. Ther., 3:661-717, 1984; Bhakdi et al., Infect. Immun., 47:52-60, 1985, the disclosures of which are incorporated herein by reference in their entirety). Group A streptococci produce streptolysin O. Streptolysin O is used in the art generally as an analytical reagent for permeabilizing cells (e.g. Razin et al., *Proc. Nat'l. Acad. Sci.* (*USA*) 91:7722-7726 (1994).

Of interest to the present invention are the disclosures of co-owned U.S. Pat. Nos. 5,576,289 and 5,736,508 which are hereby incorporated by reference. U.S. Pat. No. 5,576,289 discloses the use of streptolysin O in methods for treating disease states characterized by motor deficit including multiple sclerosis and autism. U.S. Pat. No. 5,736,508 discloses the use of streptolysin O in methods for treating scarring.

Of further interest to the present invention are the disclosures in co-owned U.S. Pat. Nos. 7,196,058 and 7,629,058 the disclosures of which are incorporated by reference herein which disclose streptolysin O as having effects on MMP-2 which is a keratinocyte cell surface marker and is believed to be involved in the breakdown of extracellular matrix in normal physiological processes. Keratinocyte migration is involved in wound healing.

SUMMARY OF THE INVENTION

The invention provides methods of inhibiting microglial cell migration in the brain of a mammalian subject in need thereof comprising administering an effective amount streptolysin O (SLO) wherein microglial migration is inhibited.

More specifically, the invention provides methods of inhibiting microglial cell migration, such as to the site of an injury, in the brain of a mammalian subject suffering from a Tau pathology selected from the group consisting of primary age-related tauopathy, chronic traumatic encephalopathy, progressive supranuclear palsy, corticobasal degeneration, frontotemporal dementia, parkinsonism linked to chromosome 17, Lytico-Botig disease, ganglioglioma, gangliocytoma, meningioangiomatosis, postencelphalitic parkinsonism, subacute sclerosing panencephalatis, lead encephalopathy, tuberous sclerosis, Hallervorden-Spatz disease and lipofuscinosis and Beta-amyloid diseases selected from the group consisting of Alzheimer's disease and prion mediated diseases, CNS injuries selected from the group consisting of spinal cord injury and traumatic brain injury (TBI), neurodevelopmental diseases selected from the group consisting of schizophrenia, Amyotrophic Lateral Sclerosis, cerebral ischemia and hematoma in the brain.

While gliosis is part of the inflammatory response to injuries in the CNS it is believed that gliosis may stimulate scarring in the brain which can prevent normal neuronal growth and axonal extensions.

In one aspect of the invention, the method inhibits microglial cell migration in a subject suffering from traumatic brain injury (TBI) and by doing so is effective in alleviating one or more symptoms of a traumatic brain injury (TBI) in a subject is provided. In some embodiments, the method comprises administering streptolysin O to the subject in an amount effective to alleviate one or more symptoms of the TBI. In some embodiments, the one or more symptoms of TBI are selected from the group consisting of amnesia, confusion, disorientation, difficulty remembering new information, headache, dizziness, blurry vision, nausea, vomiting, ringing in the ears, trouble speaking coherently and changes in emotions and sleep patterns. According to one aspect of the invention, both acute and chronic forms of traumatic brain injury are treated as disclosed below.

In another aspect of the invention, the method inhibits microglial cell migration in a subject suffering from a hematoma in the brain. While hematomas can occur in a variety of organs microglial cells are found only in the CNS. Thus, the method of the invention is useful in the treatment of a variety of hematomas including but not limited to subgaleal hematomas, cephalohematomas, epidural hematomas, subdural hematomas, subarachnoid hematomas and othematomas.

The streptolysin O is, in some embodiments, formulated in a number of pharmaceutically-acceptable carriers or excipients including, but not limited to, water, saline, albumin, dextrose or any other pharmaceutically acceptable excipient known in the art. The precise dose will vary among patients and may readily be determined by those of ordinary skill in the art. In some embodiments, the streptolysin O is administered in a dosage amount ranging from about 0.00016 ng to about 3200 ng per dose and is preferably formulated in a liquid vehicle. In some embodiments, the streptolysin O is provided at a concentration ranging from 0.016 ng to about 32 ng per dose or from about 0.16 ng to about 3.2 ng per dose.

According to one aspect of the invention the administration of SLO blocks increases in microglia cells in the hippocampus following trauma. According to a further aspect of the invention the administration of SLO maintains or restores memory following brain trauma.

Additional aspects, features and variations of the invention will be apparent from the entirety of this application, including the detailed description, and all such features are intended as aspects of the invention. It should be understood, however, that the detailed description and the specific examples are given by way of illustration, and that the many various changes and modifications that will be apparent to those familiar with the field of the invention are also part of the invention.

Aspects of the invention described with the term "comprising" should be understood to include the elements explicitly listed, and optionally, additional elements. Aspects of the invention described with "a" or "an" should be understood to include "one or more" unless the context clearly requires a narrower meaning.

DETAILED DESCRIPTION OF THE INVENTION

Figure 1A:
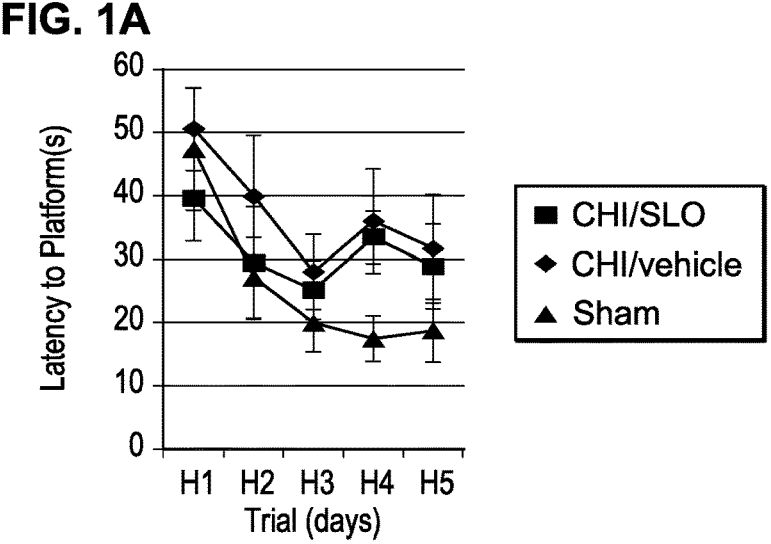
FIGS. 1A, 1B and 1C depict the results in a mouse head trauma model measuring the time for sham, control injured and treated injured mice to find a submerged platform.

The present application relates to the discovery that streptolysin O is capable of alleviating a variety of ailments associated with microglial migration including traumatic brain injury including both the acute and chronic effects of such brain injury. According to one aspect of the invention the administration of SLO to subjects suffering from traumatic brain injury appears to block the increase in microglia cells in the hippocampus following trauma as well as maintaining or restoring memory following trauma.

Method of Use

In one aspect, a method for alleviating one or more symptoms of a traumatic brain injury (TBI) in a subject comprising administering streptolysin O to the subject in an amount effective to alleviate one or more symptoms of the TBI. In some embodiments, the one or more symptoms of TBI are selected from the group consisting of amnesia, confusion, disorientation, difficulty remembering new information, headache, dizziness, blurry vision, nausea, vomiting, ringing in the ears, trouble speaking coherently and changes in emotions and sleep patterns. In some embodiments, the one or more symptoms of TBI are selected from the group consisting of amnesia, confusion, disorientation, difficulty remembering new information, headache, dizziness, blurry vision, nausea, vomiting, ringing in the ears, trouble speaking coherently and changes in emotions and sleep patterns.

The term "streptolysin O" as used with respect to the methods described herein means streptolysin O which has been modified by oxidation to eliminate cytotoxic effects while retaining important cholesterol binding characteristics on the cell membrane. Streptolysin O is readily oxidized in solution and is commercially available (Sigma Product Catalog).

The dose of streptolysin O administered to the subject can be determined by the physician, taking into account, age, sex, weight, etc. of the subject. In some embodiments, the streptolysin O is administered in a dosage amount ranging from about 0.00016 ng to about 3200 ng per dose. In some embodiments, the streptolysin O is provide at a dose of about 0.016 ng, or about 0.02 ng, or about 0.05 ng, or about 0.1 ng, or about 0.2 ng, or about 0.3 ng, or about 0.4 ng, or about 0.5 ng, or about 1 ng, or about 10 ng, or about 20 ng, or about 40 ng, or about 60 ng, or about 80 ng, or about 100 ng, or about 500 ng, or about 1000 ng, or about 1500 ng, or about 2000 ng, or about 2500 ng, or about 3000 ng per dose. In some embodiments, the streptolysin O is provided at a dose ranging from 0.016 ng to about 32 ng per dose or from about 0.16 ng to about 3.2 ng per dose.

In some embodiments, the administered dose of streptolysin 0 is at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 65, 70, 75, 80, 85, 90, 95, 100, 110, 120, 130 or more International units. In one embodiment, the administered dose of streptolysin O is about 1.6 ng (about 4 International units). In some embodiments, streptolysin O is administered 1, 2, 3, 4, 5, 6, 7, 8, 9, 10 or more times daily for a period of 1, 2, 3, 4, 5, 6 or more weeks. Additional therapy may be administered on a period basis, for example, daily, weekly or monthly.

The term "effective amount" as used herein, refers to an amount of the therapy (i.e., streptolysin O) sufficient to treat, ameliorate, or prevent the identified disease or condition (or symptoms associated with the disease or condition), or to exhibit a detectable therapeutic, prophylactic, or inhibitory effect. The effect can be detected by, for example, an improvement in clinical condition or a reduction in symptoms. The precise effective amount for a subject will depend upon the subject's body weight, size, and health; the nature and extent of the condition. Therapeutically effective amounts for a given situation can be determined by routine experimentation that is within the skill and judgment of the clinician.

The subjects treated in the methods disclosed herein in its many embodiments are desirably human subjects, although it is to be understood that the principles of the presently disclosed subject matter indicate that the presently disclosed subject matter is effective with respect to invertebrate and to all vertebrate species, including mammals, which are intended to be included in the term "subject."

Formulation and Route of Administration

The streptolysin O described herein may be formulated in pharmaceutical compositions with a pharmaceutically acceptable excipient, carrier, or diluent.

In some embodiments, the pharmaceutical compositions are formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions comprises in various aspects a therapeutically effective amount of at least one composition as described herein, together with one or more pharmaceutically acceptable excipients.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using suitable dispersing or wetting agents and suspending agents. The sterile injectable preparation may also be a sterile injectable solution or suspension in a non-toxic parenterally acceptable diluent or solvent, such as a solution in 1,2-propane-diol.

Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

Example 1

The following Example demonstrates the ability of SLO to alleviate a variety of ailments associated with traumatic brain injury (TBI) in the brains of ex-NFL players. In these cases, TBI was likely induced by multiple concussions.

Six former NFL players with a history of TBI which manifested itself with symptoms such as diminished executive functions, social relationships, forgetfulness, confusion and anxiety volunteered to undergo therapy by administration of SLO. Each volunteer was provided with a supply of SLO and instructed to take one drop of SLO four times daily—after meals and before bed. Each drop of SLO was to be administered sublingually. Each drop contained 1.6 ng (about 4 units) of oxidized SLO. Players were monitored by telephone conversation on a monthly basis.

Five of the six volunteers reported improvements such as enhanced cognition, better memory, increased ability to articulate, better sleep patterns, improved emotional stability, and overall improved quality of life. The sixth participant was lost to follow-up and it cannot be confirmed that he was compliant with administration of the experimental therapy. No adverse events were reported.

During further followup, another of the original volunteers withdrew from the trial but four of the original six subjects continue to take SLO drops, although frequency of administration was generally reduced. Nevertheless, those four subjects reported continued benefit of the therapy with no regression.

Example 2

The following Example is directed to treatment of a female subject suffering from the effects of a traumatic brain injury as the result of an automobile accident thirty (30) years ago when the subject was age 19. The subject developed a dropped soft pallet because of nerve damage resulting from the original accident which rendered her speech difficult to understand. The subject suffers from anxiety, impaired short term memory, loss of organization skills and reduced cognition skills.

The subject was treated with sublingual administration (under the tongue and on the floor of the mouth) of a single drop (0.05 mL) composition comprising 2 units of oxidized streptolysin O in phosphate buffered saline four times daily. The subject did not swallow for 15 seconds after administration of the composition and did not eat or drink anything for five minutes.

At 40 days the subject appeared calmer that previously, was reading more and took on some new interests watching the morning stock reports and other television programs.

At 70 days the subject had taken on further new interests and remained calmer and less anxious.

At 106 days the subject had continued to develop new interests, took more pleasure in her appearance and reading and had developed a more positive attitude toward life.

At 141 days she remained calm and her condition still remained superior to that from when she initiated treatment with the composition of the invention.

At 173 days the subject's short term memory appeared to have improved with the ability to recall events occurring earlier in the day and within the immediate past week. Her comments on happenings were observed to be more insightful and appropriate and she remained calmer.

At 216 days the subject was able to initiate art therapy, kayak with friends and write email correspondence without supervision which had not been possible prior to initiation of the therapy.

Example 3

The following Example is directed to treatment of traumatic brain injury in a mouse model. Control and test animals were subjected to head trauma daily (for 4 or 7 days) according to the method described in Mannix et al. Annals of Neurology, Vol., 74, No. 1 1 pp. 65-75 (2013). Experimental group received doses of SLO (4 IU) subdural in AM and PM of all days of the experiment.

One aspect of the model focuses on the ability of the test animals to find a submerged (hidden) platform that offers a safe haven upon which they can stand after being injured and placed in a pool of water. This test measured learning process and memory of the tested mice. Non-injured mice (the sham controls) took about 30 seconds to locate the pad on test day one. This time dropped during successive test days.

Figure 1B:
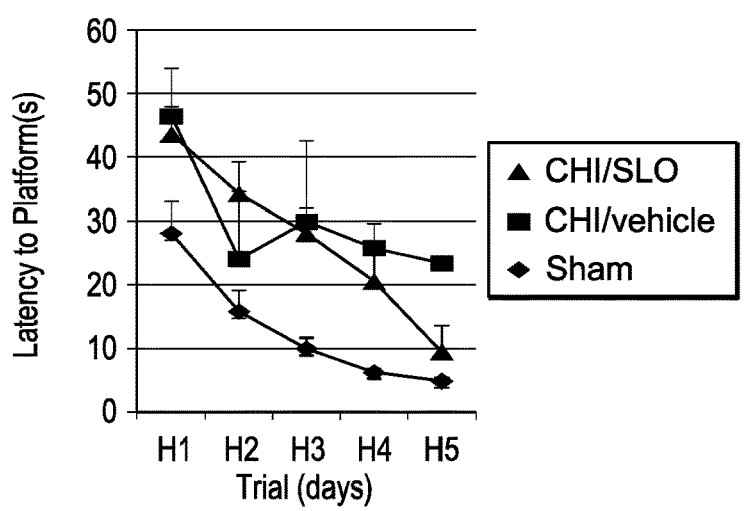
Figure 1C:
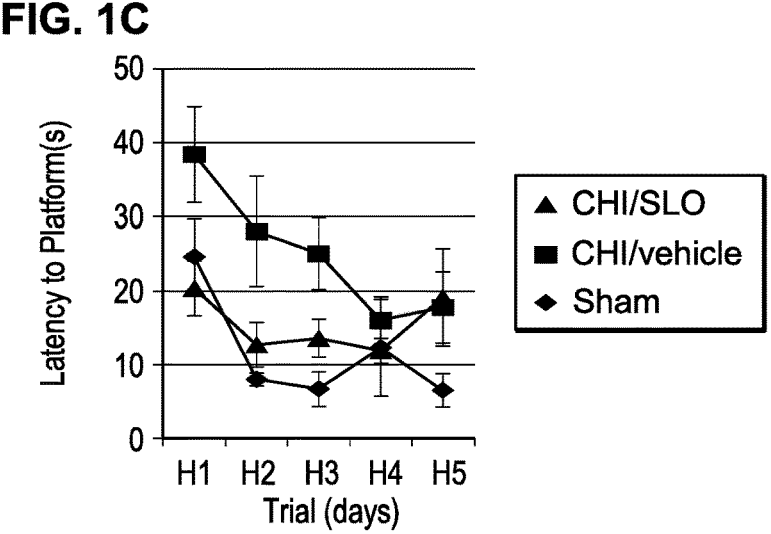

Two other groups of mice then received controlled blows to the head and were then treated by administration of the streptolysin O (SLO) therapeutic composition or a placebo. As indicated in FIGS. 1A, 1B and 1C the placebo treated animals generally performed worse than the sham mice while the SLO treated animals generally performed in superior manner to the control injured mice. In another limited set of experiments (not shown) it was not clear that SLO treated injured mice outperformed control injured mice in probe trials testing memory or visible trials testing vision.

Example 4

According to this example a histopathologic evaluation was conducted on the brains of mice subjected to traumatic brain injury. Mice received 7 "hits" each day for 7 days, +/−SLO twice daily (4 IU subcutaneous). The SLO treatment was continued for days 7 more days and then the animals were sacrificed and hippocampus dissected. Proteins were extracted from tissue and proteins separated by gel electrophoresis and blotted. Proteins specific to astrocytes (GFAP) and microglia (IBA1) were identified by western blotting and scanned (normalized to beta actin). The GFAP (astrocyte marker) and IBA1 (microglial marker) experiments showed no differences in GFAP or dIBA1 expression in the cortex among sham, vehicle treated injured mice and SLO treated injured mice. Nevertheless, IBA1 expression in the cortex seemed reduced in the hippocampus in SLO treated injured mice compared with vehicle treated injured mice suggesting that inflammation may be suppressed by SLO.

Further, a histopathologic evaluation of the brains of the animals from the several groups showed that the administration of the SLO therapeutic composition inhibited microglia migration in the hippocampus, which is the portion of the brain associated with memory, compared with administration of placebo.

Without intending to be bound by any particular theory of invention it is believed that the inhibition of the microglia migration in the hippocampus might prevent potentially harmful inflammation that would be anticipated in the non-treated situation. It has further been observed that SLO down-regulates MMP-2 and MMP-9 which are inducers of inflammation and that SLO inhibits keratinocyte migration in a fashion that may be similar to the observed microglial inhibition.

According to another aspect of the invention it is observed that the chronic form of traumatic brain injury is different from the acute form. The administration of SLO might also function to reverse the gliosis that has occurred to form scar-like tissue that interferes with intercellular communication in the brain. Such a therapeutic activity might then function to reverse collagen-associated scarring in patients with long-term (multiple year and multiple decade) histories of traumatic brain injury.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method of inhibiting microglial cell migration in the brain of a mammalian subject suffering from traumatic brain injury (TBI) comprising administering an effective amount of streptolysin O (SLO) wherein microglial migration is inhibited.

2. The method of claim 1 which treats one or more symptoms of TBI.

3. The method of claim 2, wherein the one or more symptoms of TBI are selected from the group consisting of amnesia, confusion, disorientation, difficulty remembering new information, headache, dizziness, blurry vision, nausea, vomiting, ringing in the ears, trouble speaking coherently and changes in emotions and sleep patterns.

4. The method of claim 1 wherein the TBI is a chronic injury.

5. The method of claim 1 wherein the TBI is an acute injury.

6. The method of claim 1, wherein the SLO is administered by a route of administration selected from the group consisting of sublingual, bucal, oral drench, subcutaneous, intradermal, intravenous, intrathecal, inhalation, topical and intramuscular administration.

7. The method of claim 1, wherein the SLO is administered sublingually.

8. The method of claim 1, wherein the SLO is administered in a dosage amount ranging from 0.00016 ng to 3200 ng per dose.

9. The method of claim 1, wherein the SLO is administered at a dosage from 0.016 ng to 32 ng per dose.

* * * * *